(12) United States Patent
Batz et al.

(10) Patent No.: US 6,521,744 B1
(45) Date of Patent: Feb. 18, 2003

(54) 2- OR 3-DIMENSIONAL GEOMETRIC STRUCTURES

(75) Inventors: Hans-Georg Batz, Tutzing (DE); Troels Koch, Kobenhaven S. (DK); Henrik Frydenlund Hansen, Rodovre (DK)

(73) Assignee: PNA Diagnostics A/S, Glostrup (DK)

( * ) Notice: Subject to any disclaimer, the term of this patent is extended or adjusted under 35 U.S.C. 154(b) by 0 days.

(21) Appl. No.: 09/656,759

(22) Filed: Sep. 7, 2000

Related U.S. Application Data

(62) Division of application No. 09/087,514, filed on May 28, 1998, now Pat. No. 6,310,179.

(30) Foreign Application Priority Data

May 30, 1997 (EP) .......................................... 97 108 670

(51) Int. Cl.$^7$ .......................... C07H 19/00; C08L 77/00; C12Q 1/68; C07K 7/00; C07K 5/00
(52) U.S. Cl. .................... 536/22.1; 536/26.6; 536/18.7; 530/333.32; 530/338; 435/6
(58) Field of Search ............................... 536/26.6, 22.1, 536/2.66, 18.7; 435/6; 530/333.32, 338

(56) References Cited

U.S. PATENT DOCUMENTS 5,561,071 A 10/1996 Hollenberg et al.
5,714,331 A * 2/1998 Buchardt et al.

OTHER PUBLICATIONS

Carter, P., et al., "Humanization of an anti–p185(HER2) Antibody for Human Cancer Therapy." Proc. Natl. Acad Sci. USA, vol. 89, pp. 4285–4289, May (1992), Immunology.*

Carayannopoulos, L., et al., "Recombinant Human lgA Expressed in Insect Cells." Proc. Natl. Acad Sci. USA, vol. 91, pp. 8348–8352, Aug. (1994), Immunology.*

Seeman, et al. "DNA nanoconstructions", J. Vac. Sci. Technol., vol. 12, No. 4, 1994, pp. 1895–1903.

Kallenbach, et al. "An immobile nucleic acid junction constructed from oligonucleotides", Nature, vol. 305, 1983, pp. 829–931.

Nielsen, et al. "sequence–Selective Recognition of DNA by Strand Displacement with a Thymine–Substituted Polyamide", Advancement of Science, vol. 254, No. 5037, 1991, pp. 1497–1500.

Du et al. "Synthesis of a DNA Knot Containing Both Positive and Negative Nodes", J. Am. Chem. Soc., vol. 114, 1992, pp,. 9652–9655.

Wang et al. "Peptide Nucleic Acid Probes for Sequence–Specific DNA Biosensors", J. Am. Chem. Soc., vol. 118, 1996, pp. 7667–7670.

* cited by examiner

*Primary Examiner*—Jeffrey Fredman
*Assistant Examiner*—Christine Maupin
(74) *Attorney, Agent, or Firm*—Arent Fox Kintner Plotkin & Kahn

(57) ABSTRACT

Nucleic acid analogs provide a particularly useful tool for the preparation of complex polymeric structures of defined geometry because they are relatively stable to reaction conditions for the preparation of such structures and provide the opportunity to induce reactive groups which would not be possible with usual nucleic acids.

9 Claims, 1 Drawing Sheet

2- OR 3-DIMENSIONAL GEOMETRIC STRUCTURES

Figure 1:
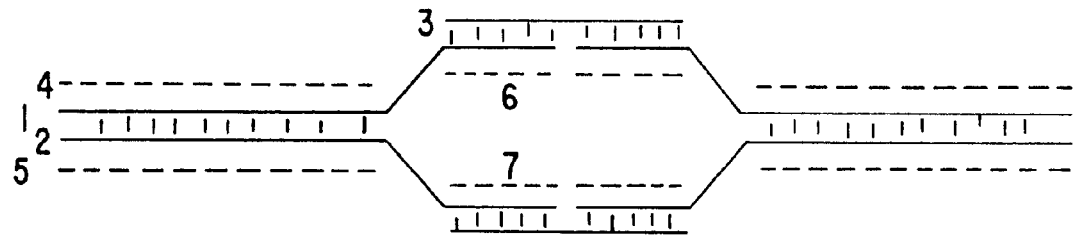

This is a divisional of application Ser. No. 09/087,514 filed May 28, 1998 now U.S. Pat. No. 6,310,179.

Subject of the present invention is a method for constructing a 2- or 3-dimensional defined polymeric geometric structure from oligomeric elements, such geometric structures as well as the use of nucleic acid analogues in assembling of supramolecular structures of defined form.

Living organisms are build from biomolecules particularly by defined self association of such biomolecules (lipids, protein complexes and DNA double helix). Such supramolecular structures occurring in living organisms are relatively unstable outside of these organisms, because the biomolecules have only limited affinity and are biologically degradable.

Lehn (Science 260, 1762–1763, 1993) describes the use of artificial self assembled complexes from low molecular weight organic molecules and metal ions.

It is further known that holes can be created in Longmuir-Blodget-layers during cluster formation. Such artificial systems are based on the association of uniform molecules having no or small differences.

In nature complex structures are made up from macro molecules of different tertiary structures, based upon uniform basic structures like amino acids and nucleotides. Nucleic acids of complementary sequence form helical chains which can form later in-vivo special structures and networks.

In Angew. Chem. Int. Ed. Engl. 1997, 36, 7, 735–739 a supramolecular structure based on macrocycles is disclosed. In J. Am. Chem. Soc. 1997, 119, 852–853, control of stereochemistry in supramolecular architecture is described.

In J. Vac. Sci. Technol. A 12(4), 1895–1903, there is described the self-assembly of DNA molecules to form a 2-dimensional latice. Such latices are formed using DNA molecules the nucleotide sequence of which is chosen such that four or more of such DNA molecules have a preferred assembly to form a junction. There is explicit explanation in this document how the sequences of the DNA molecules involved has to be chosen. Further there is at least theoretical disclosure how a 3-dimensional object, like a cube, can be created from 6 cyclic DNA molecules. Again, the sequences of the DNA molecules are chosen such that the structure is stabilized and defined by the formation of double stranded DNA along the edges of the cube.

In DE-A-3924454 and U.S. Pat. No. 5,561,071 there is described the use of self-assembled double stranded DNAs for forming conducting elements, for example elements used in electronic chips. The disclosure of this reference is incorporated by reference into the present specification.

The supramolecular structures prepared by self-assembly of DNA have now been found to be so unstable under in vitro conditions that, for example electronic chips prepared by them are not reliable.

In WO 92/20702 there are disclosed purely synthetic oligomeric molecules which are capable of binding to complementary nucleic acids with very high affinity. This can be used for either therapy within the human body or in the diagnosis of nucleic acids in vivo or in vitro. Peptide nucleic acids (PNAs) as described in this reference are characterized by having a non-naturally occurring backbone having attached nucleobases at defined positions, such that these nucleobases can hydrogen bond to the complementary bases on a DNA strand, thus forming a double or triple stranded complex.

It was therefore an object of the present invention to provide high molecular weight supramolecular structures in a more reliable way.

It was an alternative or additional object of the present invention to provide more stable high molecular weight supramolecular structures in a predictable way.

In a further object of the present invention to provide new materials based on supramolecular structures in an intended way, which can be used in computer chips, in roboting, such as robot arms in nanometer scale, in new materials/polymers with conductivity and/or insulator properties.

Subject of the present invention is therefore a method for constructing a 2- or 3-dimensional defined polymeric geometric structures comprising the steps of combining a first oligomeric element having bound recognition elements with a second oligomeric element having bound recognition elements capable of recognizing the recognition elements of said first oligomeric element at binding conditions, wherein said recognition elements are heterocyclic moieties recognizing other recognition elements via hydrogen bonding and wherein said recognition elements of said first and second oligomeric element are bound to spaced defined locations of a peptide bond containing backbone. A further subject of the present invention are such polymeric geometric structures.

FIG. 1 shows the structure of a self-assembled 2-dimensional geometric structure prepared by self-assembly of three different peptide nucleic acids.

A defined geometric structure according to the present invention is a structure having a defined expansion and which can be drawn schematically. Examples of such defined geometric structures are latices, junctions, cubes and branched molecules as described in the above mentioned prior art. Therefore, the invention can be used in nano-engineering to create intended structures. While the prior art describes DNA for making up the structure, the present invention is directed to the use of oligomeric elements comprising a peptide like bond containing backbone. The geometric structures preferably contain at least one branching point. A branching point is defined to be the location where three or more arms meet. At least one of these arms comprises a segment wherein one strand of this arm is bound to a strand of a further oligomeric element. The oligo- or polymeric geometric structure according to the present invention comprise at least two oligomeric elements. However, it is preferred that such a structure contains 6 or more, preferably between 8 and 1 Million oligomeric elements. In this definition oligomeric structures will contain from 2 to 20 and polymeric structures more than 21 oligomeric elements. These oligomeric elements can be of the same kind, for example only differing in the sequence of the recognition elements, preferably, however, the oligomeric elements are of a different kind, for example differing in sequence and in molecular structure, for example some of them being modified further or being based on different backbones or moieties attached.

An oligomeric element according to the invention is defined to contain affinity moieties, such as alkyl, aryl, aromatic or/and heterocyclic moieties recognizing other heterocyclic molecules via van-der-Waals interaction, $\pi$-stacking, water exclusion or hydrogen bonding. Said affinity moieties are bound to spaced defined locations of a polyamide backbone. The backbone is generally a non-naturally occurrin backbone. The backbone preferably contains repetitive monomeric subunits, such subunits being covalently bound together, preferably using amide bond formation. While it is much preferred to use only one kind of monomeric subunit in the backbone, it is possible to use different subunits and/or different bonds within the backbone either mixed individually or as stretches containing several identical subunits, as described in WO 95/14706, EP 700928, EP 646595 and EP 672677.

Oligomeric elements having both a non-natural backbone part as well as an excessable oligonucleotide and can be used to postmodify the geometric structure after assembly. Thus, it is possible to attach further mononucleotide units to the end of the oligomeric unit, for example as described in EP 720615.

Preferred oligomeric elements, such as peptide nucleic acids (PNAs), are described in WO 92/20702. Such compounds comprise a containing polyamide backbone bearing a plurality of heterocyclic moieties that are individually bound to amine atoms located within said backbone.

Preferred peptide nucleic acids are shown in formula I:

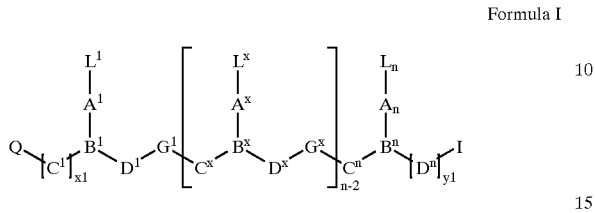

Formula I wherein n is an integer of from at least 3, x is an integer of from 2 to n−1, each of $L^1$–$L^n$ is a ligand independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups, heterocyclic moieties, reporter ligands and chelating moieties, at least one of $L^1$–$L^n$ containing a primary or secondary amino group;

each of $C^1$–$C^n$ is $(CR^6R^7)y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, ($C_1$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined below, and $R^5$ is hydrogen, ($C_1$–$C_6$)alkyl, hydroxy, ($C_1$–$C_6$) alkoxy, or ($C_1$–$C_6$)alkylthio-substituted ($C_1$–$C_6$)alkyl or $R^6$ and $R^7$ taken together complete an alicyclic or heterocyclic system; or $C^1$–$C^n$ is CO, CS, $CNR^3$;

each of $D^1$–$D^n$ is $(CR^6R^7)_z$ (preferably $CR^6R^7$, $CHR^6CHR^7$ or $CH_2CR^6R^7$) where $R^6$ and $R^7$ are as defined above;

each of y and z is zero or an integer from 1 to 10, the sum y+z being at least 2, preferably greater than 2, but not more than 10;

each of $G^1$–$G^{n-1}$ is $-NR^3CO-$, $-NR^3CS-$, $-NR^3SO-$ or $-NR^3SO_2-$, in either orientation, where $R^3$ is as defined below;

each of $A^1$–$A^n$ and $B^1$–$B^n$ are selected such that:

(a) $A^1$–$A^n$ is a group of formula (I/A), (I/B), (I/C) or (I/D), and $B^1$–$B^n$ is N or $R^3N^+$; or (b) $A^1$–$A^n$ is a group of formula (I/D) and $B^1$–$B^n$ is CH;

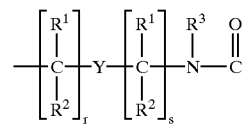

Formula I/A

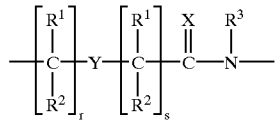

Formula I/B

Formula I/C

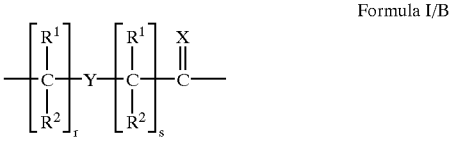

Formula I/D wherein:

X is O, S, Se, $NR^3$, $CH_2$ or $C(CH_3)_2$;

Y is a single bond, O, S or $NR^4$;

each of p and q is zero or an integer from 1 to 5, (the sum p+q being preferably not more than 5);

each of r and s is zero or an integer from 1 to 5, (the sum r+s being preferably not more than 5);

each $R^1$ and $R^2$ is independently selected from the group consisting of hydrogen, ($C_1$–$C_4$)alkyl which may be hydroxy- or ($C_1$–$C_4$)alkoxy- or ($C_1$–$C_4$) alkylthio-substituted, hydroxy, ($C_1$–$C_4$)alkoxy, ($C_1$–$C_4$)alkylthio, amino and halogen; and each $R^3$ and $R^4$ is independently selected from the group consisting of hydrogen, ($C_1$–$C_4$)alkyl, hydroxy- or alkoxy- or alkylthio-substituted ($C_1$–$C_4$)alkyl, hydroxy, ($C_1$–$C_6$)-alkoxy, ($C_1$–$C_6$)-alkylthio and amino;

Q and I are independently selected from the group consisting of $NH_2$, $CONH_2$, COOH, hydrogen, ($C_1$–$C_6$)-alkyl, O—($C_1$–$C_6$)-alkyl, amino protected by a amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers as well as nucleic acid binding moieties and each of x1 and y1 is an integer of from 0 to 10.

Most preferred nucleic acid binding compounds comprise at least one monomeric subunit of the general formula II:

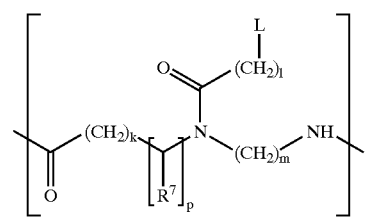

(II)

wherein

L is a ligand as defined above for $L^1$–$L^n$, k, l and m is independently zero or an integer from 1 to 5, p is zero or 1, and $R^7$ is selected from the group consisting of hydrogen and the side chains of naturally occurring alpha amino acids.

Preferred recognition elements are nucleobases, like naturally occurring nucleobases, like A, G, C, T and U, rare bases, like inosine, 5-methylcytosine or thiouracil, as well as any non-naturally occurring analogues, like 7-deaza-dGTP, bromothymine and azaadenines. These recognition elements are able to recognize corresponding recognition elements on another oligomeric element, as known in the art. The present invention thus provides the possibility to create intended structures, with high specificity, for example based on sequences of recognition elements.

Hydrogen bonding is a way of binding, particularly as occurring between two strands of a nucleic acid, including Watson-Crick base pairing and Hoogsteen base pairing.

The recognition elements are bound to specified and constant locations on the backbone, preferably separated by between 4 and 8 intervening atoms. The preferred atom of attachment is a nitrogen atom.

The oligomeric elements used in the present invention can be prepared by methods as described in the above documents. The use of peptide like bonds within the backbone provides a good opportunity of easy synthesis using DNA or peptide synthesizers. When prepared, the oligomeric elements can be coupled to other moieties that are intended to be included in the geometric structure of the present invention, such as recognizing moieties, moieties that can be recognized, catalytically active moieties, labels or chemically reactive or activatable moieties. Recognizing moieties and moieties that can be recognized are moieties that can recognize and preferably bind to an other component. Examples are immunologically reactive compounds, antibodies, antigens, and preferably peptide epitomes containing moieties, like polyhaptens or cyclic peptides. Such moieties can also connect oligomeric elements, for example can one end of a cyclic peptide be linked to a first oligomeric element and the other end be linked to a second oligomeric element. This can be accomplished by synthesizing such conjugate before introducing into the polymeric structure, for example in a peptide synthesizer.

Catalytically active moieties are enzymes, preferably polymeric enzymes, for example aggregates of a large numbers of enzymes, bound together covalently. A variety of labels can be conjugated to the oligomeric element, for example fluorescence labels, dyes, or even metals or other solid particles. Preferred are reactive groups.

Reactive groups useful in the present invention are groups that can bind covalently to other groups, like recognizing moieties as defined above, preferably, groups that can be used to crosslink oligomeric elements or to bind any further moieties to the oligomeric elements before or after assembly of the polymeric structure. Such crosslinking moieties are for example arylazide, acylazide, diazirines, ketones, quinones, and psoralens. The preparation of oligomeric elements useful in the present invention is disclosed in detail in WO 92/20702 and U.S. Pat. No. 5,539,082. These references are incorporated herein.

As mentioned above the use of chimeric elements offers the possibility to extend shorter oligomeric elements by, for example, enzymatic extension reactions using mononucleotides. Another example of extension is chemical ligation of oligomeric subunits by reaction of a thioester on one oligomer with a thiol group on another oligomer, also containing an amino group close to the thiol group. The thioester exchange will link the two oligomers together. Then the amino group on the second oligomer will interchange the newly formed thioester to form an amide bond (Canne et al. J. Am. Chem. Soc. 1996, 118, 5891–5896). Another example of chemical ligation is the combination of an activated group of one oligomer subunit with a functional group on the same or another oligomeric subunit. This reaction can be performed by an activated carboxylic acid derivative on one oligomer and an amino group on the same or on an other oligomer.

Covalent joining of two segments can also be performed by using duplexes/triplexes having overhanging ends. The overhanging end of one duplex can then hybridize with the overhanging end of the other duplex/triplex, thus forming a duplex with double length. By employing a recognition moiety capable of making a crosslink (see above) the overhanging region can be covalently joined.

In a preferred mode of the method of the present invention at least two oligomeric elements are combined under conditions suitable for binding the oligomeric elements together by hydrogen bonding via the recognition elements. Suitable conditions for peptide nucleic acid are disclosed in WO 92/20703. One of the biggest advantages of the use of PNA in the present invention is that they can bind via base pairing to nucleic acids or other PNA oligomers in non-physiological media, for example in water without or with very low salt content.

PNA having bound chelating moieties are disclosed in WO 95/14708. These PNA oligomers further give the opportunity to bind metal ions (thus doping the geometrical structure with metal ions) for increasing electric conductivity within such oligo/polymeric structure. PNA having attached peptide moieties are disclosed in WO 95/16202. These compounds provide the opportunity to functionalize the geometric structure according to the present invention by post modification, for example enzymatic modification, or to build up new or additional association structures, like the use of antibodies to bind to peptide antigens by making a "bridge" structure.

Contrary to the recognition between nucleic acids, the distances of affinity moieties in the sequence can be chosen more freely, because it is not necessary that, especially in the case wherein the first and second oligomeric element are made up of the same kind of backbone, to recognize nucleic acids, as in methods for nucleic acids determination. Therefore, the present invention provides a much more flexible way of constructing geometric structures than structures prepared by using naturally occurring DNA. However, it may be preferred, that the distances between recognition elements within the segments of each oligomeric element are at least compatible or similar, and preferably within segments of oligomeric elements designed for binding together via hydrogen bonding, and the distances between said recognition elements are such that π-stacking and/or water exclusion of the recognition elements is still possible. Favorable interstrand interaction can be readily determined by determining the melting temperatures ($T_m$) of the double/triple stranded product produced by the first and second oligomeric element. The higher the $T_m$, the higher the interstrand affinity.

A 1-dimensional structure is a structure having no branching points, i.e. a linear structure.

A 2-dimensional structure according to the present invention is for example a structure having linear structures oriented in one layer, wherein said linear structures are preferentially connected to each other at branching points. A 2-dimentional structure can be straight, curved or ring formed. Rings may be linked together as in a chain or catenants.

A 3-dimensional structure can be defined as a 2-dimensional structures extended into more than one layer or containing more than one branching point. An example of 3-dimensional structure is a cube, a tube, or spiral shaped structure.

The geometric structures constructed according to the present invention are of high interest in the preparation of nano-structures and nano-engineering. The development of nano-structures is of interest because of the small space required for advanced instruments and the requirements of small amounts of material compared to macroscopic structures. The development into nano-structures can best be explained in the field of computers. While the first computers required large space because the underlying hardware had extended dimensions, development of semiconductor technology made it possible to create computers having very high capacity but requiring only limited space. It is now recognized that the presently used photolithographic modes for preparing computer chips limits the further downscaling of chips. Nano-structures as produced in the present invention now provide for these smaller dimensions necessary for the construction of even downscaled computer chips.

This possibility now enables the construction of wires or conducting elements as small, preferably in diameter, as double stranded nucleic acid analogues, the dimensions of which are in about the same range as double stranded nucleic acids. However, by including single stranded segments into the geometric structure, it is possible to even downscale any wires to the strength of single stranded nucleic acid analogues or even simple organic molecules, for example carbohydrids.

The geometric structures according to the present invention can be prepared by combining two or more oligomeric elements (either extended or not extended), under conditions wherein they can bind in a specific or non-specific way using the recognition elements. When specific joining is intended, then natural or non-natural nucleobases can be used which are capable of base pairing (a process generally called hybridization). When non-specific joining is intended, then duplex formation takes place preferentially by interstrand π-stacking and/or water exclusion.

In a first application of the geometric structure of the present invention the structure is therefore used as a mask to create a defined pattern, for example on a surface. Fixating of the nucleic acid analogue may be by passive adsorption to the surface but can also be performed by bond formation (ionic or covalently) between the analogue and the surface. Such bond can be formed by thermal or photochemical means.

The pattern created on the surface can be used to cover or coat part of or all remaining parts (for example on said surface), not covered by said structure by a material, for example with doped silicon, for example using metallo organic chemical vapour deposition, removing the geometric structure containing the assembled oligomeric elements, and then applying to the now unprotected part of the surface a second material, for example a conductor as doped gallium arsenide or doped silicon. Therefore the geometric structure of the present invention can be designed as a network or a lattice, thus enabling the defined production of chips. A part of said conceptual considerations for preparation of computer chips from networks or latices can be transferred in analogy from U.S. Pat. No. 5,561,071 which to this end is incorporated herein by reference.

The use of nucleic acid analogues and especially peptide nucleic acids in this field has considerable advantages. Nucleic acid analogues are more stable than nucleic acids under the conditions of coating surfaces with metals. Especially in the field of the preparation of computer chips where one break within the geometric structure, for example by breaking a glycosidic or phosphate bond in one of the nucleic acids, would have the severe consequence on the electric current that then could not flow through the "wire".

PNA are nucleic acid analogues that in preferred embodiments do not contain glycosidic or/and phosphate bonds, and as such is much more stable, which reduces the risk of strand breaks considerably compared to nucleic acids. This makes the chips prepared using nucleic acid analogues far more reliable in use. In addition nucleic acid analogues, as PNA, can be modified as described above in a more flexible way, due to their relatively flexible way for introducing chemically reactive sites.

In a second embodiment, the supramolecular geometric structures prepared according to the present invention can be used as scaffolds for electron transfer and thus lead electric current themselves. It was now determined that double strands constructed using oligomeric elements of the present invention, particularly if an uninterrupted π-stack of heterocyclic moieties or other aromatic/conjugated systems is contained within the double strand, can act as a nanostructural conductor for electrons (see for example U.S. Pat. No. 5,591,578 or C & EN, Feb. 24, 1997, Angew. Chem. Int. Ed. Engl. 1997, 36, 7, 735–739 or J. Am. Chem. Soc. 1997, 119, 852–853). In a simple application, it is thereby possible to connect two macroscopic electrodes via an electron transfer scaffold, "wire", composed of a double strand of oligomeric elements. Such electrodes can be metallic surfaces, to which one of the oligomeric elements of the geometric structure is attached directly, for example covalently, or indirectly, for example by absorbing the geometrical structure or an oligomeric element to the electrode surface. Immobilization of PNA to a carbon electrode is described in J. Am. Chem. Soc. 1996, 118, 7667–7670. The content of this publication is incorporated by reference as it is directed to the preparation of a nucleic acid analogue attached to an electrode and the measurement of potentiograms of double stranded nucleic analogues bound to the electrode.

Using the present invention, it is possible to connect two electrodes, each of them being prepared according to the prior art, by assembling a geometric structure according to the invention. This can be made in a linear way, as described above, or can include more partial surfaces, for example separated electrodes, which can be connected in a directed way using specific sets of oligomeric elements. For example it is possible to provide a surface with an array of electrodes, each electrode having attached a specific oligomeric element or even an extended polymeric structure and thereafter connecting selected electrodes by connecting the oligomeric elements to create a geometric structure according to the invention or arms of an extended geometric structure of one electrode with an oligomeric element or an extended geometric structure of another selected electrode. In this way, customer-designed electrodes and structures can be prepared. Such devices containing an array of electrodes can be produced by selectively applying one or more small droplets of a solution containing these structures or oligomeric elements to the surface of each electrode. Any excess of compounds may be washed away. Thereafter the connections between the selected electrodes can be established as described above.

It is further possible to postmodify any geometrical structure produced according to the method of the present invention by crosslinking or even enzymatic extension. Crosslinking can be effected by irradiating a geometric structure having incorporated a photochemically active moiety, like acridine, arylazide, acylazide, diaziridines, ketones, quinones or psoralenes with light of an appropriate wavelength for activating the crosslinking reaction. Crosslinking can also be made by thermochemical means, like in polymer preparation by radical or electrophilic chain reactions using double bond containing moieties, like acrylates or styrenes, or by activation of functional groups like carboxylic acids which, when activated, are capable to react with other functional groups like amines. In this way additional branching points or even interstrand/duplex stabilization of double stranded parts can be accomplished. It is further possible to dope any negatively charged moieties in the geometrical structure by ions, for example silver ions, analogously to the method disclosed in Nature, vol. 391, p. 775, 1998, to which reference is made for the preparation and use of such doped structure.

Three dimensional structures can be made in a consecutive manner by adding 2-dimensional structures on top of each other, which forms an integrated multilayer structure forms structure.

Modification of the conformation of a 3-dimensional structure can be done by using special photochemical groups, like azabenzenes, stilbene, which isomerise (e.g. cis/trans isomers) upon irradiation.

The 2- or 3-dimensional structures can be preformed in solution before addition to e.g. a solid phase or made directly on the surface by first adding one strand of a duplex to the surface and then adding the complement strand so the duplex is formed on the solid surface. The precipitated structure may retain its structure as in solution, e.g. tertiary form as a helix, or it may change structure on the surface from a helix to a duplex with the form as a ladder.

Furthermore another advantage of using PNA is that the molecules allow for certain sequences to form stable triplexes (PNA-DNA-PNA, or PNA-PNA-PNA). This binding motif allows to prepare much more integrated structures than e.g. DNA.

Further subject of the present invention therefore is the use of compounds containing or being prepared by using a monomeric subunit of the general formula

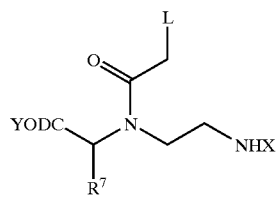

wherein

X is an amino protecting group and Y is a carboxyl protecting group, $R_7$ is a moiety containing a functional group with a positive or negative charge, for example a carboxyl group, phosphate group or ammonium group, or is a moiety capable of complexing or chelating metal ions, or is a reactive group, for example for inducing covalent crosslinking, for example mercapto, maleinimido, quinone, nitrene or carbene or as described above and L is an affinity moiety preferably heterocyclic moiety or a reactive aromatic moiety, for example an aromatic azide or quinone for the preparation of supramolecular structures of defined form on the basis of base sequence specificity or base non-specificity, particularly for the construction of new materials (e.g. new polymers), capable of base pairing to nucleobases, conducting networks and computer chips, and for crosslinking such structures, or binding recognizing moieties to such structures.

Nucleic acid analogues provide a particularly useful tool for the preparation of complex polymeric structures of defined geometry because they are relatively stable to reaction conditions for the preparation of such structures and provide the opportunity to introduce reactive groups which would not be possible with usual nucleic acids.

A further advantage of the use of nucleic acid analogues is the possibility to provide them with better solubility in organic solvents and their relatively lower solubility in water compared to nucleic acids. Furthermore, the lipophilic nature of the nucleic acid analogues provides much higher affinities for many surfaces.

In the following a specific example for a method of the present invention is outlined.

EXAMPLE 1
Preparation of Nucleic Acid Analogues

Peptide nucleic acid is nucleic acid analogue having a N-(2-aminoethyl)-glycine backbone, with the bases linked to the central N-atom by a 2-carboxylmethyl group. PNA is prepared by the methods disclosed in WO 92/20702 and U.S. Pat. No. 5,539,082. The sequences are given in each example.

EXAMPLE 2
Assembly of a Double Fork Geometric Structure Containing 6 Nucleic Acid Analogues According to example 1 the following peptide nucleic acid molecules are prepared:
1. 
   H-TCA-CGT*-ACC-TAG-TCT*CT-TGC-AT*G-CAT-NH$_2$
2. H-CGA-TGC-T*AC-TCTCT*-CTA-GGT*-ACG-TGA-NH$_2$
3. (H-GTA-GCA-T*CG)$^2$-(ATG-CAT*-GCA)$^1$-NH$_2$
   ($^2$Complementary to segment in bold in 2, and $^1$ complementary to segment in bold in 1.

The following peptide nucleic acid molecules were prepared as control molecules
4. H-CTA-GGT*-ACG-TGA-NH$_2$ (Complementary to underlined segment in 1.)
5. H-TCA-CGT*-ACC-TAG-NH$_2$ (Complementary to underlined segment in 2.)
6. H-GTA-GCA-T*CG-NH$_2$ (Complementary to bold segment in 2.)
7. H-ATG-CAT*-GCA-NH$_2$ (Complementary to segment in bold in 1.)

T* indicates that the T-monomers at that position is composed of lysine containing backbone.

Molecules 1, 2, 3 are designed to form an oligomeric structure containing 6 PNA molecules as oligomeric elements (each of the three is contained twice). The sequences are chosen such that there is specific and predetermined binding of the oligomeric elements 1, 2 and 3. The geometric structure formed has two branching points and four double stranded segments.

Control Hybridizations

Measurement of the melting temperature ($T_m$) shows sequential hybridization of the individual control parts indicating that all segments are capable of hybridizing. Thus, hybridizing the 12-mers, control segments 4 and 5, to the complementary segments in either 1 or 2 gives a clear transition at ca. 72° C. Hybridizing the 9-mer control segments (6 and 7) to either 1 or 2 gives a transition at ca. 60° C. Hybridization of the joining segment (3) to either 1 or 2 gives a transition at ca. 65° C. These experiments indicate that the stem has a $T_m$ of about 73° C. (12 mer) and the fork part has a lower $T_m$ of ca. 60° C. (9 mers).

Formation of Supramolecular Structures

Hybridization 1 and 2 to each other (single fork formation, joining two molecules) gives a very clear transition at 73° C. with a large ΔOD just as the control segments showed. Mixing 1, 2 and 3 (forming the double fork, joining 6 molecules) gives a clear transition at 73° C. and a weak transition around 50–60° C. ΔOD in this experiment is the largest measured. This experiment indicates that the two hybridized stem parts (dimers, formed by duplex formation) of the structure can be joined by the overlapping PNA (3). The overall structure is anticipated to be the intended "double fork". In addition to the Tm measurements the increased ΔOD of the overall complex indicated that a larger structure is formed.

The supramolecular structures can be visualised by AFM (atomic force microscopy)(ref. Hansma, H. G. & Hoh, J. Annu. Rev. Biophys. Biomol. Struct. 23, 115–139 (1994); Bustamante, C. & Rivetti, C. Annu. Rev. Biophys. Biomol. Struct. 25, 395–429 (1996); Han, W., Linsay, S. M., Dlakic, M. & Harrington, E. R. Nature, 386, 563.). The structures can e.g. be prepared in solution and then applied to the readable surface, or prepared by consecutive adding the building blocks to the surface. Furthermore neutron diffraction can give indications of the average size of supramolecular structures in solution.

We claim:

1. A method of constructing a predetermined two or three dimensional geometric structure comprising at least three oligomeric elements, the method comprising binding the at least three oligomeric elements to form a forked structure, each of the at least three oligomeric elements independently comprising a peptide bond-containing backbone and having a plurality of recognition elements bound to the backbone at spaced and predetermined locations thereon, wherein each of the plurality of recognition elements independently comprises a heterocyclic moiety, and the at least three oligomeric elements are bound to each other via the recognition elements through hydrogen bonding, van-der-Waals interaction, π-stacking or a condensation reaction.

2. The method of claim 1, wherein at least six oligomeric elements are bound to each other in said binding step.

3. The method of claim 1, wherein eight to one million oligomeric elements are bound to each other in said binding step.

4. The method of claim 1, wherein the at least three oligomeric elements each comprise a peptide nucleic acid comprising a polyamide backbone bearing a plurality of heterocyclic moieties which are bound at spaced and predetermined locations to amine atoms located within the backbone.

5. The method of claim 1, wherein the at least three oligomeric elements each comprise a peptide nucleic acid of formula I Formula I

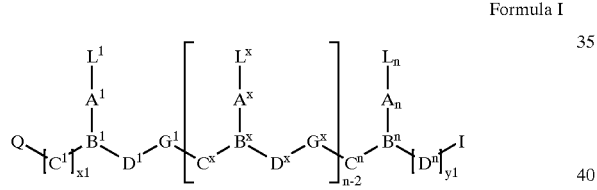

wherein n is at least 3;

x is 2 to n−1;

each of $L^1$–$L^n$ is independently selected from the group consisting of hydrogen, hydroxyl, $C_1$–$C_4$ alkanoyl, a naturally occurring nucleobase, a non-naturally occurring nucleobase, an aromatic moiety, a DNA intercalator, a nucleobase binding group, a heterocyclic moiety, a reporter ligand and a chelating moiety, wherein at least one of $L^1$–$L^n$ contains a primary or secondary amino group;

each of $C^1$–$C^n$ is independently selected from the group consisting of CO, CS, $CNR^3$ wherein $R^3$ is as defined below, $(CR^6R^7)_y$, $(CHR^6CHR^7)_y$ and $(CR^6R^7CH_2)_y$, wherein $R^6$ is hydrogen and $R^7$ is selected from the group consisting of one of the side chains of naturally occurring alpha amino acids, or $R^6$ and $R^7$ are independently selected from the group consisting of hydrogen, $C_1$–$C_6$ alkyl, aryl, aralkyl, heteroaryl, hydroxy, $C_1$–$C_6$ alkoxy, $C_1$–$C_6$ alkylthio, $NR^3R^4$ and $SR^5$, wherein $R^3$ and $R^4$ are as defined below and wherein $R^5$ is selected from the group consisting of hydrogen, $C_1$–$C_6$ alkyl, hydroxy, $C_1$–$C_6$ alkoxy and $C_1$–$C_6$ alkylthio-substituted $C_1$–$C_6$ alkyl, or $R^6$ and $R^7$, taken together with the atoms to which they are bound, form an alicyclic or heterocyclic system;

each of $D^1$–$D^n$ is independently selected from the group consisting of $(CR^6R^7)_z$, $(CHR^6CHR^7)_z$ and $(CH_2CR^6R^7)_z$, wherein $R^6$ and $R^7$ are as defined above;

each of y and z is zero or an integer from 1–10, wherein y+z is at least 2;

each of $G^1$–$G^{n-1}$ is independently selected from the group consisting of —$NR^3CO$—, —$CONR^3$, —$NR^3CS$—, —$CSNR^3$—, —$NR^3SO$—, —$SONR^3$—, —$NR^3SO_2$— and —$SO_2NR^3$—, wherein $R^3$ is as defined below;

each of $A^1$–$A^n$ and $B^1$–$B^n$ are selected such that:

(1) each of $A^1$–$A^n$ is independently selected from the group consisting of a group of formula (I/A), (I/B), (I/C) and (I/D), and each of $B^1$–$B^n$ is independently N or $R^3N^+$, wherein $R^3$ is as defined below, or (2) each of $A^1$–$A^n$ is a group of formula (I/D) and each of $B^1$–$B^n$ is CH;

Formula I/A
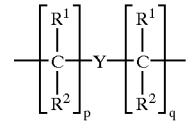

Formula I/B
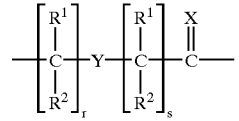

Formula I/C
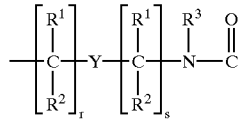

Formula I/D
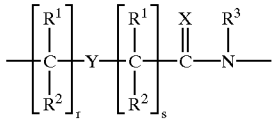

wherein

X is selected from the group consisting of O, S, Se, $CH_2$ and $C(CH_3)_2$ and $NR^3$, wherein $R^3$ is as defined below;

Y is selected from the group consisting of a single bond, O, S and $NR^4$, wherein $R^4$ is as defined below;

each of p and q is independently zero or an integer from 1 to 5;

each of r and s is independently zero or an integer from 1 to 5;

each of $R^1$ and $R^2$ is independently selected from the group consisting of hydrogen, hydroxy, $C_1$–$C_4$ alkoxy, $C_1$–$C_4$ alkylthio, amino, halogen and $C_1$–$C_4$ alkyl, which is unsubstituted or has a substituent selected from the group consisting of hydroxy, $C_1$–$C_4$ alkoxy and $C_1$–$C_4$ alkylthio; and each of $R^3$ and $R^4$ is independently selected from the group consisting of hydrogen, hydroxy, $C_1$–$C_6$ alkoxy, $C_1$–$C_6$ alkylthio, amino and $C_1$–$C_4$ alkyl, which is unsubstituted or has a substituent selected from the group consisting of hydroxy, $C_1$–$C_4$ alkoxy and $C_1$–$C_4$ alkylthio;

Q and I are each independently selected from the group consisting of $NH_2$, $CONH_2$, COOH, hydrogen, $C_1$–$C_6$ alkyl, O—$C_1$–$C_6$ alkyl, amino protected by an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside, a soluble or non-soluble polymer and a nucleic acid binding group; and each of x1 and y1 is independently zero or an integer from 1 to 10.

6. The method of claim 1, wherein at least one of the at least three oligomeric elements comprises a monomeric subunit of formula II

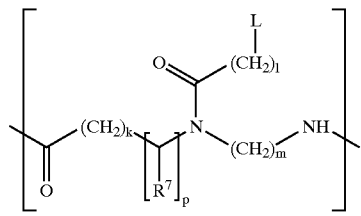

(II)

wherein

L is selected from the group consisting of hydrogen, hydroxyl, $C_1$–$C_4$ alkanoyl, a naturally occurring nucleobase, a non-naturally occurring nucleobase, an aromatic moiety, a DNA intercalator, a nucleobase binding group, a heterocyclic moiety, a reporter ligand and a chelating moiety and a ligand containing a primary or secondary amino group;

each of k, l and m is independently zero or an integer from 1 to 5;

p is zero or 1; and $R^7$ is selected from the group consisting of hydrogen and one of the side chains of naturally occurring alpha amino acids.

7. The method of claim 1, wherein sets of recognition elements are bound to each other, each set comprising a recognition element from at least two different oligomieric elements, wherein at least one recognition element from the set comprises a moiety independently selected from the group consisting of adenine, cytosine, guanine, thymine, uracil, inosine, 5-methylcytosine, thiouracil, 7-deaza-dGTP, bromothymine and azaadenine.

8. The method of claim 1, wherein sets of recognition elements are bound to each other, each set comprising a recognition element from at least two different oligomeric elements, wherein at least one recognition element from the set comprises a moiety independently selected from the group consisting of an immunologically reactive compound, an antibody an antigen and a peptide epitope-containing moiety.

9. The method of claim 1, wherein each of the plurality of recognition elements on each of the at least three oligomeric elements is separated from another of the plurality of recognition elements by between 4 and 8 intervening atoms on the backbone of the oligomeric element to which the plurality of recognition elements are bound.

* * * * *